United States Patent [19]

Bolder et al.

[11] Patent Number: 5,688,521
[45] Date of Patent: Nov. 18, 1997

[54] LACTULOSE PASTILLES

[75] Inventors: Hermann-Josef Bolder; Faruk Imer, both of Cologne, Germany

[73] Assignee: Bolder Arzneimittel GmbH, Cologne, Germany

[21] Appl. No.: 535,073

[22] PCT Filed: Apr. 28, 1994

[86] PCT No.: PCT/EP94/01344

§ 371 Date: Dec. 1, 1995

§ 102(e) Date: Dec. 1, 1995

[87] PCT Pub. No.: WO94/25002

PCT Pub. Date: Nov. 10, 1994

[30] Foreign Application Priority Data

May 4, 1993 [DE] Germany ............ 43 14 705.4

[51] Int. Cl.$^6$ .................................. A61K 9/20
[52] U.S. Cl. ............... 424/439; 424/440; 424/441; 424/464; 424/435; 514/774; 514/778; 514/779; 514/782
[58] Field of Search ............... 424/439, 440, 424/441, 464, 435

[56] References Cited

U.S. PATENT DOCUMENTS 3,860,708 1/1975 Prout .................... 424/180
3,867,524 2/1975 Ebner .................... 424/180

FOREIGN PATENT DOCUMENTS

WO93/10797  6/1993  WIPO .

OTHER PUBLICATIONS

Patent Abstracts of Japan, vol. 14, No. 403 (C–0753) Aug. 31, 1990 & JP,A,02 150 240 (Tsutomu) Jun. 8, 1990.

Chemical Abstracts, No. 18093, vol. 121 (Mamoru, et al) & JP A6 040 922, (Morinaga Milk Industry Co. Ltd.) Feb. 15, 1994.

Walter Rahn, "Pharmaceutical Forms of Sucking", (translated from Pharmazeutische Zeitung, pp. 2214, 1982) pp. 1–14, dated Oct. 14, 1982.

Chemcial Abstracts, vol. 113, 130924s, 1990.

*Primary Examiner*—Thurman K. Page
*Assistant Examiner*—James M. Spear
*Attorney, Agent, or Firm*—Banner & Witcoff, Ltd.

[57] ABSTRACT

Object of the invention is a single dose form of application for lactulose in the form of pastilles based on at least partially or completely water soluble natural and/or synthetic polymers selected from gums, alginates, carrageen, starch, pectin, and gelatin comprising lactulose as active substance, as well as a process to prepare the said pastilles.

11 Claims, No Drawings

LACTULOSE PASTILLES

This application is a 371 of PCT/EP94/01344 filed Apr. 28, 1994 published as WO94/25002, Nov. 10, 1994.

The invention relates to sucking pastilles on the basis of certain natural or synthetic polymers comprising 4-O-β-D-galactopyranosyl-D-fructose (lactulose) as an active substance.

By the term pastilles there are generally understood—see also W. Rahn, Pharmazeutische Zeitung, pp 2214–2218 (1982) preparations which can be sucked or chewed in the mouth. Namely, it is differentiated essentially between tablets, hard candies and gum pastilles (also designated as gum candies).

The processes for producing these forms of administration are basically distinguished from each other.

Tablets are pressed in tablet machines. To this end, the tablet mass has to be prepared by mixing and granulating. Several authors already have dealt with granulating methods for active substances difficult to process.

Candies are prepared by mixing saccharose and glucose syrup, cooking the resulting mixture at about 130° C., and removing most of the water from the mass in vacuo to a residual water content of from 0.5 to 2%. To the highly viscous candy mass cooled down to about 85° C. are added the active substances and flavors and admixed by kneading. With continuous cooling, the candy mass is drawn into strands, shaped, and cut in tapered rollers and other candy machines. Due to the viscosity of the candy mass, the distribution of the active substance is known to be rather non-uniform.

Gum pastilles are prepared by initially dissolving in an agitator vessel hydrocolloids, e.g., gum arabic, together with saccharose, glucose syrup, sorbitol, xylitol, and others in water and solving, emulsifying or suspending the active substances in this base mass. The casting composition obtained this way is cast into so called powder trays. These are, for example, flat wooden boxes having a size of 80 cm×40 cm being filled with starch, especially corn starch. The desired shapes are pressed into the smoothed powder using a stamp board and the warm casting solution is exactly metered and pumped into the thus obtained wells, whereby the cast mass is not bound with the powder. Tray by tray, 500 to 1000 pastilles in each case, is cast this way, stacked, and water is removed from the pastilles in drying chambers to about 10% residual moisture within 3 or 4 days. The pastilles produced this way are "depowdered" and then transferred to a final treatment.

Lactulose is a synthetic disaccharide from D-galactose and D-fructose obtained by alkaline lactose epimerization which has been marketed for a long time by various offerers as liver therapeutic and intestinal regulator in various forms of administration. For example, lactulose is commercially available in the form of syrup or granulate. However, pharmaceutical single-dose applications are lacking.

From Chemical Abstracts, 1990, Vol. 113, Ref. 130924s, it is known a chewing gum containing lactulose. A serious drawback of this form of administration consists in only a portion of the preparation being taken up by the human body, while the base material of the chewing gum has to be disposed of after usage.

EP-0 189 722 B1 describes a laxative composition on the basis of lactulose which is essentially obtained by adding a water soluble calcium or magnesium salt to an aqueous lactulose syrup, adjusting the pH from 2.5 to 5, and subsequently adding a pectin. Following this, the whole is agitated for at least 5 minutes and cooled down to a temperature at which the product gels. The gel obtained this way may be taken then by means of a spoon. Therefore, an exact single-dosing of the active substance is not possible.

In EP-0 189 722 B1, U.S. Pat. No. 3,860,708 and U.S. Pat. No. 3,867,534 are referred to and it is specified that in these two patent specifications in the same way it is specified in form of a common meaningless phrase that lactulose may be present not only in the preferred form of a syrup but as well in further galenic forms, which applies to gel candies. However, within the quoted publications merely medical indications are mentioned for which lactulose is said to be applicable.

The object of the present invention as compared to the art has been to provide a novel single dosable form of administration for lactulose by applying a casting process known as such from confectionery manufacture, which is superior by: the finest distribution of the active substance within the pastille, the very accurate single dosing of the active substance, a very simple handling of the active substance, and the optimal time lengthening of the active substance in the stomach by slow sucking of the pastilles without the need to dispose of portions of the form of administration after application.

The aforementioned object is performed by pastilles on the basis of at least partially or completely water soluble natural and/or synthetic polymers, selected from gums, alginates, carrageens, starch, pectin, and gelatin which form gels or viscous solutions in aqueous systems, and further adjuvants and additives, the pastilles containing lactulose as active substance.

It has been found that the water soluble lactulose may be incorporated in an extremely easy way in a finely dispersed form into pastilles on the basis of the aforementioned natural and/or synthetic polymers.

The term pastilles and particularly the term gum pastilles comprises within the meaning of the present invention those which are prepared by casting. Therefore, the pastilles of the present invention consist of differently shaped elastic formed bodies containing super finely distributed lactulose within a mixture of hydrocolloids and other adjuvants and additives. Gum pastilles are denoted as solid solutions which upon sucking are transformed back to liquid solutions. By means of the present invention it is possible to achieve an exact single dosage of the pastille with a relatively careful processing of the ingredients. With the above mentioned, at least partially or completely water soluble natural and/or synthetic polymers it is possible to achieve a particularly good incorporation of lactulose as it is possible to work at relatively low temperatures. Thus, a particularly homogeneous distribution of the active substance in the total composition is formed allowing the dosage of the active substance with a standard deviation in the range from 0.5 to 2%. Moreover, according to the process of the present invention it is possible to produce relatively high concentrated lactulose pastilles.

Especially preferred natural and/or synthetic polymers within the meaning of the present invention are known by the term "hydrocolloids" as well. Especially preferred are the gums selected from gum arabic, gelatin and tragacanth. In the same way, adjuvants and additives are preferably selected from sugar and/or sugar substitutes, hydrogenated fats, stearic acid, paraffins, oligosaccharides and/or dextran. Especially preferred saccharides are saccharose and/or glucose syrup.

Corresponding pastilles with other active substances are as such known in the art by the term "gum pastilles". These derive their names from the raw material gum arabic incorporated therein. Also within the meaning of the present invention this hydrocolloid is preferably used as a base material as it imparts good sucking properties to the pastille.

Besides the polymers, the base mass contains particularly flavor carriers like sugar and/or sugar substitutes as the patient should suck or chew the pastille. Accordingly, it is necessary that the pastilles have such a good taste that these are not refused or even swallowed. To improve the taste, as known as such in the art, there are used corresponding adjuvants such as saccharose or their substitutes such as fructose hydrogenated glucose syrup, sorbitol, mannitol and/or xylitol as well as known sweeteners. Besides, there can be used also flavor correcting agents and essences as well as ethereal oils, thereby combining therapeutic effect and flavor improvement.

The relative amounts of each of the necessary ingredients of the pastilles are less critical. Therefore, the base mass contains, for example, from 2 to 80% by weight of the polymers, based on the total mass of the pastilles. Especially preferred is an amount of from 25 to 60% or gum arabic or from 10 to 60% by weight of gelatin, based on the total mass of the pastilles, respectively.

In a further preferred embodiment of the invention, pastilles contain 20 to 50% by weight of sugar and/or sugar substitutes, based on the total mass of the pastilles, whereby sugar or sugar substitutes may be substituted completely or partially by lactulose. The amount of lactulose may be varied within a wide range in the inventive pastilles. Preferably, the amount of lactulose, based on the total prescription, should be as large as possible. Consequently, within the meaning of the present invention it is especially preferred to select the amount of lactulose within the range of 20 to 80% by weight, particularly 40 to 60% by weight, based on the total pastille mass.

Commercially available preparations like granulate or syrup containing lactulose as active substance normally contain from 3 to 6 g lactulose per application dose. Therefore, a particularly preferred embodiment of the present invention provides pastilles containing an amount of 2 to 10 g, especially from 3 to 6 g lactulose. Normally, the weight of pastilles prepared this way is from about 3 to about 12 g, especially from 5 to 10 g.

Another embodiment of the present invention consists in the process for the preparation of the pastilles. Hereby, particularly the above defined polymers are contacted with water and other adjuvants and additives with forming a gel or a viscous solution. Subsequently, lactulose is suspended, emulsified or dissolved in the thus obtained base mass and this liquid mass is cast into forms, dried at room temperature or at elevated temperatures, especially from 40° C. to 70° C., preferably 40° C. to 50° C., removed from the form and transferred to a final treatment.

For example, at the beginning of the preparation process gelatin and saccharose are dissolved in water and emulsified or suspended with lactulose. This drug mixture is cast into so called powder trays and dried as described previously, separated from the powder and subjected to final treatment. The particular advantages of the inventive pastilles and of the process of manufacturing them consist of a minor temperature load of the adjuvants and additives and of the complete homogeneity thereof in the coating mass allowing a high accuracy of the dosage of the active substance.

We claim:

1. Sucking pastilles comprising, based on from 2 to 80% by weight, based on the total mass of the pastilles, at least partially or completely water soluble natural polymers, synthetic polymers, or both selected from the group consisting of gums, alginates, carrageen, starch, pectin, and gelatin which polymers are suitable to form gels or viscous solutions in aqueous systems, and sugar substitutes selected from the group consisting of fructose, sorbitol, mannitol, xylitol, hydrogenated glucose syrup, and sweeteners, and the pastilles further comprising 4-O-β-D-galactopyranosyl-D-fructose (lactulose) as an active substance.

2. Pastilles according to claim 1, wherein the gums are selected from the group consisting of gum arabic, gelatin and tragacanth.

3. Process for the preparation of sucking pastilles having; based on from 2 to 80% by weight; based on the total mass of the pastilles; at least partially or completely water soluble natural polymers; synthetic polymers, or both, which polymers are suitable to form gels or viscous solutions in aqueous systems, and additional adjuvants and additives, and 4-O-β-D-galaetopyranosyl-D-fructose (lactulose) as an active substance, comprising a) contacting at least partially or completely water soluble natural, synthetic polymers, or both selected from the group consisting of gums, alginates, carrageen, starch, pectin, and gelatin, with water and sugar subsitutes selected from the group consisting of fructose, sorbitol, mannitol, xylitol, hydrogenated glucose syrup, and sweeteners to form a gel or a viscous solution, and emulsifying, suspending, or dissolving lactulose in the gel or viscous solution, b) the gel or viscous solution is cast into forms, to form the pastilles and c) the pastilles are dried at room temperature or elevated temperature.

4. Process according to claim 3, wherein the pastilles are dried at a temperature ranging from 40° C. to 70° C.

5. Pastilles according to claim 2, containing from 25 to 60% by weight of gum arabic, from 10 to 60% by weight of gelatin, or both, based on the total mass of the pastilles.

6. Pastilles according to claim 1, containing from 20 to 50% by weight of sugar substitutes, based on the total mass of the pastilles.

7. Pastilles according to claim 1, containing from 20 to 80% by weight of the lactulose, based on the total mass of the pastilles.

8. Process according to claim 3, wherein in b) the forms are stamped into powder trays by means of stamping boards.

9. Process according to claim 4, wherein the pastilles are dried at a temperature ranging from 40° C. to 50° C.

10. Process according to claim 3, wherein the dried pastilles are removed from the form.

11. Pastilles according to claim 7, containing from 40 to 60% by weight of lactulose, based on the total mass of the pastilles.

* * * * *